United States Patent [19]

Simpson et al.

[11] Patent Number: 5,047,040

[45] Date of Patent: Sep. 10, 1991

[54] ATHERECTOMY DEVICE AND METHOD

[75] Inventors: John B. Simpson, Woodside; Richard L. Mueller, Mountain View; Peter S. Brown, Los Altos Hills; James R. Kermode, Costa Mesa, all of Calif.

[73] Assignee: Devices for Vascular Intervention, Inc., Redwood City, Calif.

[21] Appl. No.: 312,108

[22] Filed: Feb. 16, 1989

Related U.S. Application Data

[63] Continuation-in-part of Ser. No. 117,072, Nov. 5, 1987, abandoned.

[51] Int. Cl.[5] .............................................. A61B 17/32
[52] U.S. Cl. .................................. 606/159; 606/170; 604/22
[58] Field of Search .................. 604/22; 606/191-200, 606/167, 170, 180, 108, 159; 128/750-755

[56] References Cited

U.S. PATENT DOCUMENTS

| 3,384,085 | 5/1968 | Hall | 128/305.1 |
|---|---|---|---|
| 3,608,539 | 9/1971 | Miller | 128/754 |
| 3,614,953 | 10/1971 | Moss | 128/305.1 |
| 3,732,858 | 5/1973 | Banko | 128/753 |
| 3,867,943 | 2/1975 | Nordin | 128/305 |
| 3,889,657 | 6/1975 | Baumgarten | 604/22 X |
| 3,945,375 | 3/1976 | Banko | 128/6 |
| 4,030,503 | 6/1977 | Clark, III | 606/159 |
| 4,228,802 | 10/1980 | Trott | 604/105 |
| 4,273,128 | 6/1981 | Lary | 128/305 |
| 4,445,509 | 5/1984 | Auth | 128/305 |
| 4,592,341 | 6/1986 | Omagari et al. | 128/4 |
| 4,631,052 | 12/1986 | Kensey | 604/22 |
| 4,646,736 | 3/1987 | Auth | 128/303 R |
| 4,653,496 | 3/1987 | Bundy et al. | 128/305 |
| 4,664,112 | 5/1987 | Kensey et al. | 128/341 |
| 4,679,557 | 7/1987 | Opie et al. | 128/305 |
| 4,696,667 | 9/1987 | Masch | 604/22 |
| 4,728,319 | 3/1988 | Masch | 128/304 |
| 4,729,763 | 3/1988 | Henrie | 604/22 |
| 4,732,154 | 3/1988 | Shiber | 606/159 |
| 4,747,821 | 5/1988 | Kensey et al. | 604/22 |
| 4,749,376 | 6/1988 | Kensey et al. | 604/22 |
| 4,754,755 | 7/1988 | Husted | 128/305 |
| 4,772,258 | 9/1988 | Marangoni et al. | 604/22 |
| 4,857,046 | 8/1989 | Stevens et al. | 606/159 X |
| 4,883,458 | 11/1989 | Shiber | 606/159 X |
| 4,898,575 | 2/1990 | Fischell et al. | 606/159 X |
| 4,923,462 | 5/1990 | Stevens | 606/159 |

FOREIGN PATENT DOCUMENTS 0665908 6/1979 U.S.S.R. ............................. 606/159

Primary Examiner—Robert A. Hafer
Assistant Examiner—Kevin G. Rooney
Attorney, Agent, or Firm—Townsend and Townsend

[57] ABSTRACT

An atherectomy device for removing stenosis materials from a vascular vessel is provided. The atherectomy device includes a flexible tubular member, a flexible drive means disposed within the tubular member, and a cutting assembly carried by the distal extremity of the tubular member. The cutting assembly includes a collection chamber which receives a cutting bit carried by the drive means. The cutting bit is rotated to remove materials from the stenosis and cause the removed materials to be withdrawn into the collection chamber as the bit is advanced. A second embodiment of the atherectomy device includes an anchor member coaxially mounted within a tubular cutting blade at the distal end of the catheter. The anchor member is first advanced into a region of stenosis where it becomes embedded, and the tubular blade is subsequently advanced over the anchor member to sever the stenosis. The tubular blade and anchor member may be retracted within the catheter and thus used to withdraw the several material from the blood vessel.

19 Claims, 5 Drawing Sheets

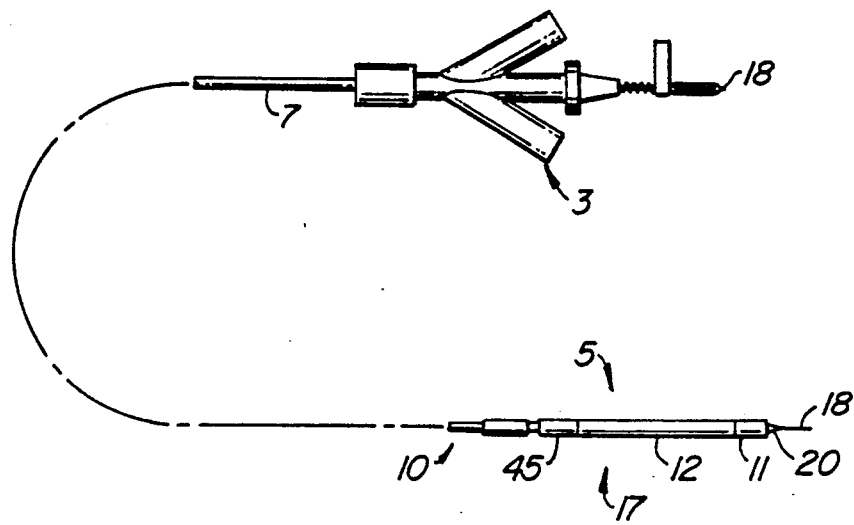
FIG._1.
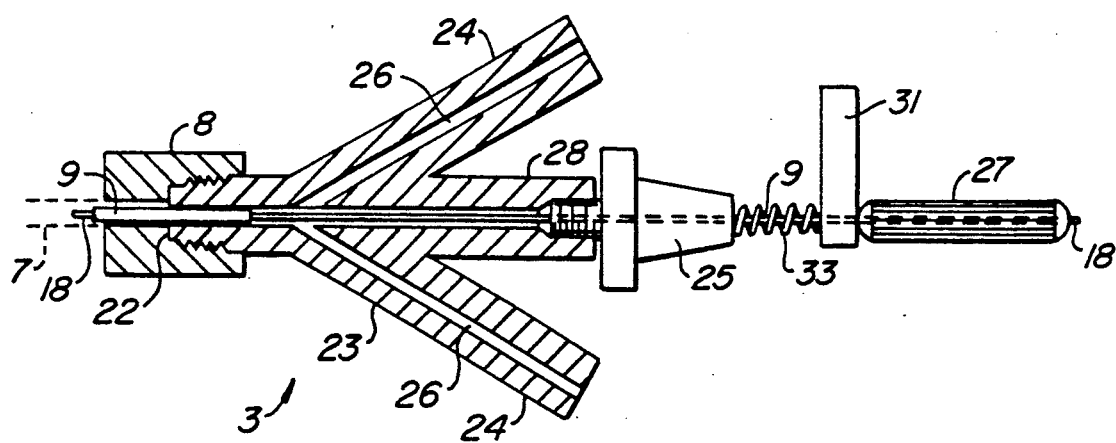
FIG._2.

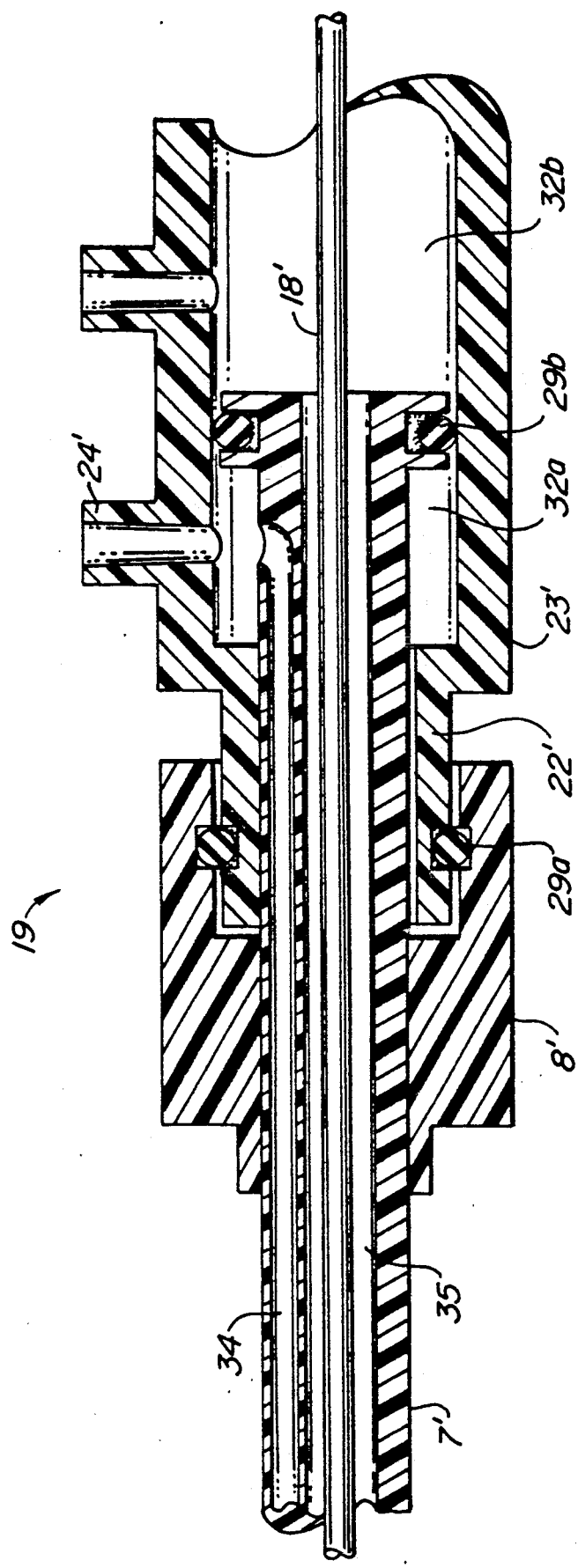
FIG_2A.

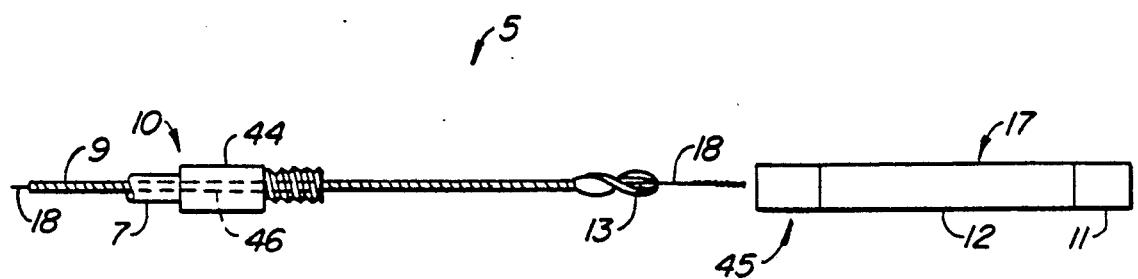
FIG._3.
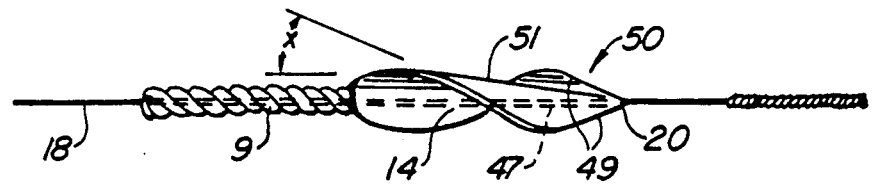
FIG._4.
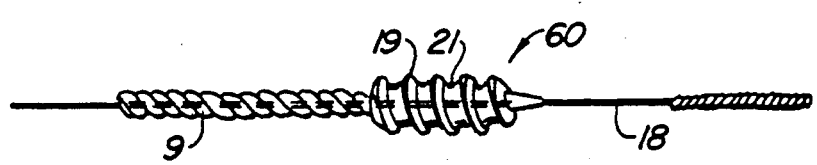
FIG._5.

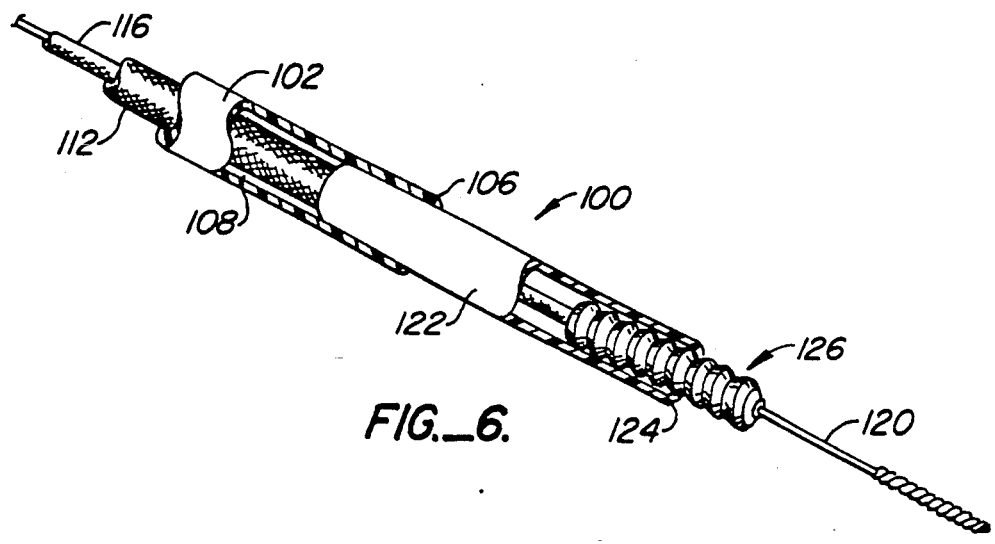
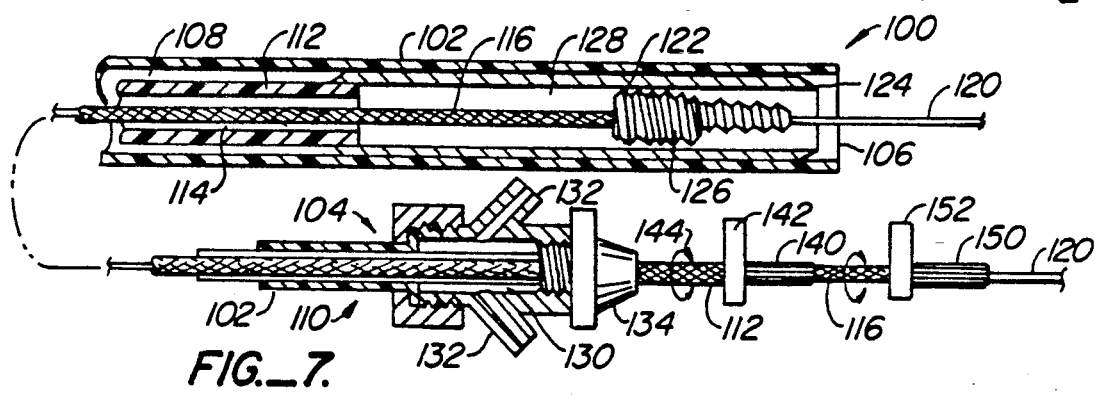
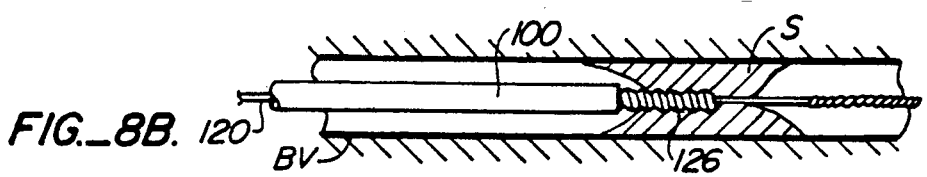
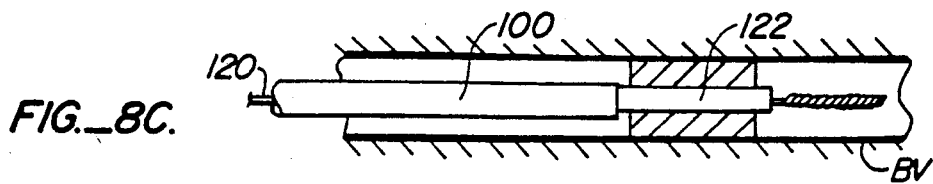

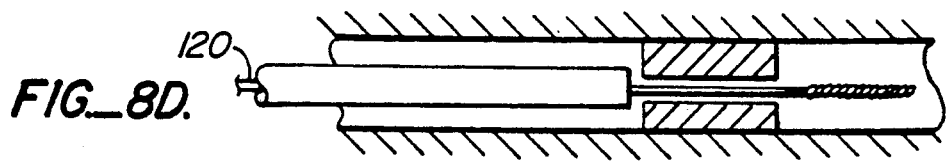
FIG._8D.
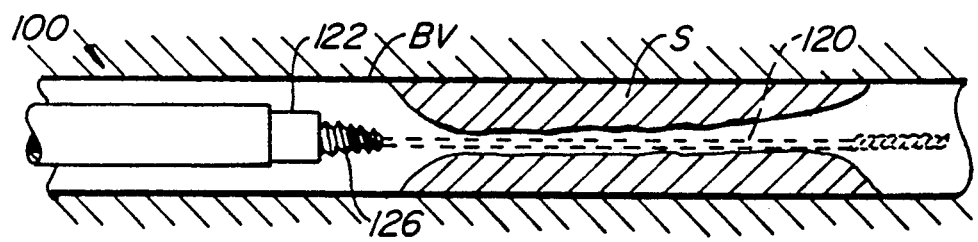
FIG._9A.
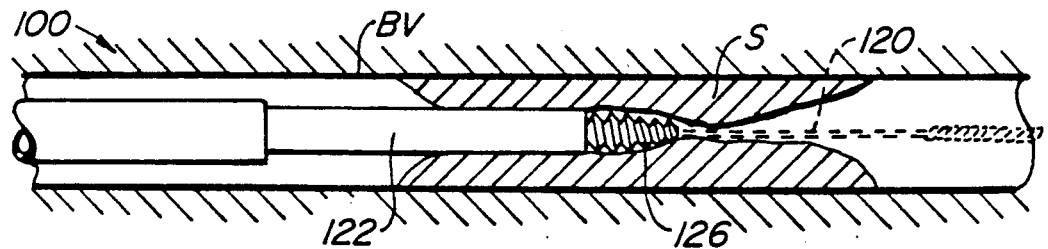
FIG._9B.
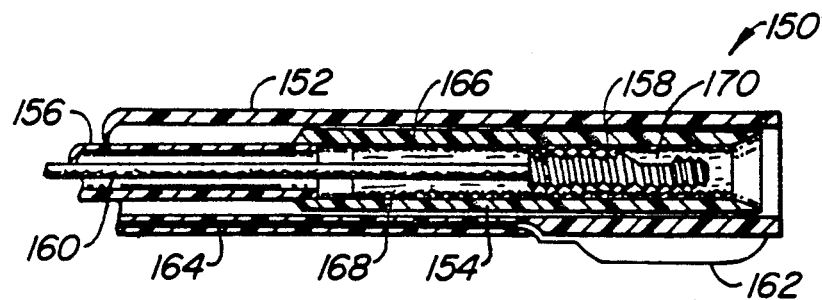
FIG._10.

ATHERECTOMY DEVICE AND METHOD

The present invention is a continuation-in-part of application Ser. No. 117,072, filed on Nov. 5, 1987, now abandoned the disclosure of which is incorporated herein by reference.

BACKGROUND OF THE INVENTION

1. Field of the Invention

The present invention relates generally to an atherectomy device and method for removing or reducing atheromas, and thrombus and plaque from within blood vessels. More specifically, the present invention discloses an improved atherectomy device that uses a distal cutter to remove atherombas, thrombus, and plaque from the walls of vascular vessels.

Coronary and peripheral vascular arteriosclerosis, known also as atherosclerosis, is a common ailment occurring in humans which involves the deposition of fatty-like substances called atheromas or plaque on the walls of blood vessels. When long term plaque build-up reaches the point of nearly totally occluding a vessel, a thrombus (clot)-type attachment can occur resulting in long segments of soft vessel occlusion. Atheromas are most common in the peripheral blood vessels that feed the limbs of the human body and the coronary arteries which feed the heart. Extended thrombus-type occlusions occur primarily in the peripheral blood vessels.

In the past, several methods have been attempted to restore normal blood flow through the affected vessels Traditionally, major surgery was the only practical means of treating occlusions. More recently, there has been substantial success in increasing the size of the flow passages within occluded vessels through the use of a dilation process known as balloon angioplasty. In the environment of extended occlusions, devices such as hot-tip probes have been used to penetrate long occlusions in order to allow subsequent entry of balloon catheters. Such penetration is necessary since angioplasty catheters have difficulty in crossing an extended occlusion on their own.

2. Description of the Background Art

A co-pending application Ser. No. 132,675 (corresponding to EPO publication 163 502) discloses an atherectomy device and method for removing at least a part of an atheroma through the use of a cutting device that is inserted into an artery where an atheroma is located. A cutting edge exposed through a cutout in the side of a substantially cylindrical housing is activated to sever a portion of the atheroma from the walls of the blood vessel. Another co-pending patent application Ser. No. 045,916 filed May 1, 1987, discloses an atherectomy device particularly suited for the removal of relatively short severe occlusions. The atherectomy catheter includes a cutter assembly having an annular cutter that is extendable beyond the confines of its housing. An expandable basket or other suitable means is provided distally of the cutter to retain the atheroma materials severed from the blood vessel walls. The disclosures of both of the co-pending applications are incorporated herein by reference.

U.S. Pat. No. 3,614,953 issued to Moss discloses a drill for clearing obstructions in arteries. The drill disclosed is carried at the distal end of a flexible drive shaft which is disposed within a pair of concentric flexible tubes. The drill bit is positioned such that its tip portion extends slightly beyond the distal end of the outer tube. Moss contemplates inserting the cutter with the cutting face exposed After the catheter has been positioned, the drill is advanced within the artery while the bit is rotated at approximately 24,000 RPM. A pair of pipes 15 and 16 communicate with inner tube 2 and outer tube 1, respectively to introduce and remove a saline solution from the vicinity of the drill bit. Saline solution is fed via a pipe and the inner tube past the flats on the bit to the cutting face and withdrawn via the outer tube and a second pipe 16. The withdrawn saline solution carries a substantial portion of the fragmented deposits loosened by the rotating bit. However, the drill bit disclosed by Moss always extends outside of its housing and does not move relative to the housing, therefore increasing the risk of traumatizing the vessel through which it passes. Additionally, it does not recognize the advantages of utilizing a guide wire when possible to substantially reduce the risk of perforating the vessel walls. Further, its vacuum-based fragment removing system is unnecessarily complicated and a non-optimal bit design is disclosed.

U.S. Pat. No. 4,445,509 discloses an alternative drilling device for removing obstructions in blood vessels. A cutting tool is mounted at the end of a flexible drive shaft which transmits torque from a motor mounted on its proximal end. The cutting tool is inserted into the blood vessel through a guiding catheter using conventional angioplasty insertion techniques. However, the cutting tool is completely exposed in this embodiment, thereby greatly increasing the risk of traumatizing the vessel. A channel is incorporated into the drive shaft and the cutting bit for systematically removing the cutting debris.

Therefore, a primary objective of the present invention is to provide an atherectomy device particularly well suited for removal of extended atheroma and thrombus-type occlusions.

Another object of the present invention is to provide an end-bladed atherectomy device that is both safe and efficacious for the removal and collection of stenosis materials such as atheromas and thrombus.

Another object of the present invention is to provide an atherectomy device capable of retaining most or all of the removed atheroma materials.

Another object of the present invention is to provide an atherectomy device capable of removing stenosis materials from a wide variety of vessels, including peripheral and coronary arteries.

SUMMARY OF THE INVENTION

To achieve the foregoing and other objects in accordance with the purpose of the present invention, an atherectomy device in the form of a catheter for removing stenosis materials from a vascular (blood) vessel is provided having a cutting assembly which can be introduced through a flexible guiding catheter or sheath. The atherectomy device includes a flexible tubular member adapted to be inserted into the vessel. A flexible drive cable disposed within the tubular member is free to move both rotationally and axially therein. A cutting assembly carried by the distal extremity of the tubular member includes a helical blade mounted in a collection chamber. The helical blade is carried by the distal extremity of the flexible drive means and serves to sever material from the stenosis and cause the severed material to be translated back into the collection chamber. A proximal actuator means in communication with proximal ends of tubular member and the drive cable is adapted to provide both axial and rotational movement to the helical blade relative to the tubular member. A flexible guide wire may also be provided.

Preferably, the helical blade is an auger bit having a plurality of inclined blade elements arranged as a helical flute. More preferably, the plurality of blade elements converge towards their distal tips at an acute angle, usually in the range of 55° to 65°. Additionally, the helical blade may include parabolic flutes.

In a method aspect of the invention, the atherectomy device is used to cut a passage through a stenosis within the vessel. The method includes the steps of inserting the device into the vessel while the helical blade is recessed within the collection chamber. The device is then advanced within the vessel until the distal end is positioned adjacent the stenosis. Desired extension of the helical cutting blade relative to the housing is then selected and the device is advanced at least partially through the stenosis thereby creating the desired passage.

In a second aspect of the present invention, the atherectomy device is a catheter having a flexible tubular member, a first flexible drive cable disposed within a central lumen of the tubular member, and a circular cutting blade secured to a distal end of the first flexible drive cable. A second flexible drive cable is disposed within a lumen of the first flexible drive cable and includes an anchor member secured to its distal end. A mechanism for separately rotating each of the drive members is provided whereby the circular cutting blade and the anchor member may be separately advanced and rotated relative to the tubular member.

The second embodiment of the atherectomy device is utilized by positioning the catheter within a blood vessel so that the distal end lies proximate a region of stenosis. The anchor member, typically a helically-threaded screw, is then advanced from the catheter and embedded into the stenosis. While the anchor member is held in place (without rotation), the circular cutting blade is advanced thereover to sever the stenosis material and entrap the severed material between the blade and the anchor member. The blade and anchor member may then be simultaneously retracted into the flexible tubular member, and the catheter removed from the patient carrying the severed stenosis. Alternatively, the second atherectomy device may be used to continuously sever stenotic material by fixing the relative axial positions of the circular cutting blade and anchor and simultaneously advancing the blade and anchor into the atheroma. By rotating the anchor (but not rotating the blade), the anchor and blade will co-act to sever the stenotic material.

The features of the present invention that are believed to be novel are set forth with particularity in the appended claims. The invention, together with further objects and advantages thereof, may best be understood by reference to the following description taken in conjunction with the accompanying drawings.

BRIEF DESCRIPTION OF THE DRAWINGS

FIG. 1 is a side elevational view of an atherectomy device incorporating the present invention.

FIG. 2 is a cut-away side elevational view of a proximal actuator assembly suitable for use with the present invention FIG. 2A illustrates a rotary seal for connecting the proximal actuator assembly to a catheter tube.

FIG. 3 is a cut-away side elevational view of the cutting assembly shown in FIG. 1.

FIG. 4 details a fluted bit ground in accordance with the teachings of the present invention.

FIG. 5 shows an alternative bit construction fashioned in accordance with the teachings of the present invention.

FIG. 6 is a perspective view of a second embodiment of the atherectomy device of the present invention, said device including both a helical anchor member and a circular cutting blade circumscribing the helical cutting member, with portions broken away.

FIG. 7 is a side elevational view of the atherectomy device of FIG. 6, illustrating the proximal housing shown in section.

FIGS. 8A-8D illustrate a method for removing stenosis according to the present invention utilizing the atherectomy device of FIG. 6.

FIGS. 9A and 9B illustrate an alternate method for removing stenosis according to the present invention utilizing the atherectomy device of FIG. 6.

FIG. 10 is a side elevational view of an atherectomy device similar to that of FIGS. 6 and 7, but incorporating certain modifications.

DESCRIPTION OF THE SPECIFIC EMBODIMENTS

Referring to FIGS. 1-3, an illustrative embodiment of the atherectomy device of the present invention includes a proximal actuator assembly 3, a cutter assembly 5, and a flexible tubular member 7 that extends between the actuator and cutter assemblies. A flexible drive member 9 (typically a tubular cable) is disposed within a central lumen of the tubular member 7 and is adapted for rotational and axial movement therein. The cutter assembly 5 is secured to a distal extremity 10 of tubular member 7 and includes a collection chamber 17 comprising a rigid housing 11 and a resilient body segment 12. Collection chamber 17 is adapted to collect the removed occlusion materials within the resilient body segment 12. A cutting bit 13 is carried by the distal extremity of drive member 9 and includes a distal tip 20 which extends forward (i.e., to the right in FIG. 1) of the housing 11 when the drive member 9 is in its fully extended position. The cutting bit 13 may also be fully retracted within the housing 11 (or even further within the collection chamber 17) by appropriate manipulation of the drive member 9.

A flexible guide wire 18 optionally extends through a lumen in drive member 9 and co-axially through lumen 47 (FIG. 4) in cutting bit 13. The guide wire 18 is movable longitudinally of the drive member 9 and is adapted to extend beyond the distal tip 20 of cutting bit 13, although it may also be retracted therein. Alternatively, the guide wire 18 may extend through a lumen (not illustrated) separately formed in tubular member 7 and aligned with an off-set lumen in distal housing 5. Additionally, a fixed guide wire attached to the distal end of tubular member 7 might alternatively be employed for positioning the catheter within the vascular system.

The proximal actuator assembly 3 is adapted to move flexible drive member 9 axially and optionally rotationally relative to tubular member 7, which in turn imparts the same motions to the cutting bit 13. A suitable proximal actuator assembly 3 (FIG. 2) includes a three arm adapter 23 threadably connected to thumb screw 25, drive shaft 27, and thumb lever 31. Tubular member 7 is anchored to distal extremity 22 of three arm adapter 23 by a compression fitting 8 (FIG. 2), while drive cable 9 is anchored in drive shaft 27. The side arms 24 of three arm adapter 23 each contain lumens 26 which may be used to inject or withdraw fluids into the blood vessel through tubular member 7. An O-ring (not illustrated) is placed between thumb screw 25 and the central arm 28 of three arm adapter 23 to seal the threaded connection therebetween. Drive member 9 passes coaxially through thumb screw 25 and is firmly adhered to drive shaft 27. Thumb lever 31 is coupled to drive member 9 just distally of drive shaft 27 in a manner such that it does not rotate with the drive member. Compression spring 33 maintains a separation between thumb lever 31 and thumb screw 25 absent pressure on the thumb lever by the user.

As illustrated in FIG. 2, the tubular member 7 is unable to rotate relative to proximal housing 23. In many cases, however, it will be desirable to provide a rotary coupling between tubular member 7 and housing 23 in order to facilitate rotation of the tubular member after it has been introduced to the vascular system. Without such a rotary coupling, it is necessary to manipulate the entire housing 23 in order to rotate tubular member 7. Rotation of tubular member would be necessary when utilizing a fixed guide wire attached to the member to allow guidance of the catheter through the vascular system.

Referring to FIG. 2A, a suitable rotary seal 19 for securing tubular member 7' to proximal housing 23' is illustrated. A female fitting 8' is secured to the tube 7' near the proximal end thereof. A male extension 22' of housing 23' is received within female fitting 8', and an O-ring 29a provides a rotary seal as the tube 7' is able to rotate relative to housing 23'. A channel flange 30 is formed at the proximal end of tube 7', and a second O-ring 29b forms a seal which divides the interior of housing 23' into a first portion 32a and a second portion 32b A first port 24' communicates with the first interior portion 32a and, in turn, with an off-set lumen 4 extending axially through the wall of tube 7'. A second port 26' communicates with the second interior portion 32b and, in turn, with central lumen 35 extending axially through the tube 7'. Catheters which employ such axial lumens are described in more detail in connection with FIGS. 7 and 10 hereinafter.

It will be appreciated that drive member 9 can be moved rotationally relative to tubular member 7 by rotating drive shaft 27. Additionally, drive member 9 can be moved axially relative to tubular member 7 by pushing thumb lever 31 toward thumb screw 25 against the pressure of spring 33. When tension is released from thumb lever 31, compression spring 33 will cause thumb lever 31 and thumb screw 25 to separate thereby causing cutting bit 13 to recess within housing 11 (or collection chamber 17). The cutting bit 13 works best when rotated at a high rate of speed. Therefore, drive shaft 27 on proximal assembly 3 is preferably splined and adapted to be attached to a motorized drive unit (not shown). A suitable motorized drive unit is disclosed in co-pending application Ser. No. 031,168 filed Mar. 26, 1987, the disclosure of which is incorporated herein by reference.

The motorized drive unit will usually be adjustable to rotational rates in the range from about 50 to 10,000 RPM, usually being in the range from about 500 to 5,000 RPM. The rotational rate selected will depend on various factors, including the nature of the stenotic material (calcified plaque generally requires faster rotation), the translational advancement rate (faster advancement generally requires more rapid rotation), the length of the cutter 13 which is exposed beyond housing 11 (with greater exposure generally requiring slower rotation to reduce material loss), and the like. Advantageously, rotational speed adjustment can be made in response to fluoroscopic or ultrasound imaging of the blood vessel during the treatment.

Guide wire 18 extends co-axially through drive cable 9 and drive shaft 27 and is free to move longitudinally therethrough. Thus, where possible, the guide wire 18 may be fed through a vessel and across an occlusion before the distal extremity of either housing 11 or bit 13, thereby guiding travel of the atherectomy device through the vessel and reducing the possibility of traumatizing the vessel wall.

Referring now in particular to FIG. 3, the construction of a first embodiment of the cutting assembly 5 will be described in more detail. Cutting assembly 5 includes a threaded male fitting 45 attached to the proximal end of collection chamber 17 and an adaptor 44 which threadably receives the fitting 45. The adapter 44 includes a central lumen 46 which allows passage of drive member 9, and cutting bit 13 is carried by the drive member within the collection chamber 17, usually within housing 11. The remainder of cutting assembly 5 is carried by the distal extremity 10 of tubular member 7. Specifically, threaded male fitting 45 is secured to a threaded end of adapter 44 carried by the distal extremity 10 of tubular member 7. Housing 11 receives cutting bit 13, as described above, and flexible body segment 12 of collection chamber 17 is positioned directly behind the housing 11. The collection chamber 17 is detachably secured to tubular member 7 by threadably engaging male fitting 45 on adapter 44. By way of example, housing 11, adapter 44 and male fitting 45 may all be formed of stainless steel or a suitable rigid plastic, while body segment 12 of collection chamber 17 may be formed from a flexible plastic or metal braid (as described further below). Any suitable adhesive may be used to secure adjoining parts.

The flexible body segment 12 of collection chamber 17 may be fashioned from any flexible material. One preferred embodiment, however, is a braided-type construction. The braided construction is formed by braiding fibers in at least a single layer of braid and coating the fibers and filling the interstices between the braided fibers to increase the strength of the braided tubing. Thus, by way of example, the braided tubing can be formed of suitable fibers, such as stainless steel having a thickness in the range of 2 to 3 mils. Thereafter, the braided fibers may be coated with a suitable plastic such as epoxy or polyurethane.

A preferred embodiment of the cutting bit 13 takes the form of a helical blade bit 50 as shown in FIG. 4. The helical blade 50 includes tip 20 and shank portion 19 which is positioned proximally of the tip. The bit 50 is formed from at least two cutting blade elements 49 which together form a helical flute 51. When distal tip 20 of bit 50 extends forward of the housing 11, occlusion materials severed by the bit will be impelled rearward by the shank portion 19 into the resilient body segment 12 of collection chamber 17.

The actual shape of the auger bit 50 is extremely important to the use of device. Particularly, it has been found that the flatter or blunter the tip 20 is, the more likely the bit will wander during cutting. This is particularly true when cutting through soft materials such as thrombus. Standard metal drilling tips typically have a pair of cutting edges 49 that meet at an oblique angle of either 118° or 134°. We have discovered that when cutting through atheroma- and thrombus-type material, particularly with a metal tip, it is generally desirable to have the cutting blade element 49 join at an acute angle. Preferably the angle formed by the cutting edges 49 is in the range of 55° to 65°.

The helix angle of the auger bit 50 also has a significant effect on the performance of the cutting bit. The helix angle refers to the angle marked "X" on FIG. 4. The greater the helix angle, the greater is the force exerted on the severed stenosis materials to travel away from the cutting tip 50 when the bit 13 is spinning. Additionally, higher helix angles generate larger vacuums at the distal tip 20 of auger bit 50 when the bit is rotated at a high rate of speed. The higher vacuums are desirable since they will cause relatively soft stenosis materials such as those found in thrombus to pull into the auger bit 50, thereby allowing the bit 50 to cut effectively with less extension beyond housing 11. The reduced extension makes the atherectomy device safer since the less exposed bit 13 is, the lower the likelihood of injuring the vessel wall. The preferred helix angle X will be in the range from about 10° to 25°.

Additionally, the helical flute 51 may be ground into a parabolic shape in order to enhance transport of the severed occlusion materials. Suitable parabolic drill bits are available from a wide variety of manufacturers, including Guhring of Brookfield, Wis.

The further flute cutting bit 13 is exposed in front of its housing 11, the greater the risk of the bit perforating the vessel wall. Therefore, it is desirable to allow the cutting bit 13 to follow guide wire 18 in order to help control the positioning of the cutting bit 13 within the vessel. The guide wire 18 greatly reduces the risks of an exposed bit 13 traumatizing the vessel. However, it is not always possible to push the guide wire across the occlusion without risking damage to the vessel. This is particularly true in extended and partially calcified occlusions. Therefore, cutting bit 13 may be retracted within housing 11 to prevent the cutting bit 13 from damaging the blood vessel particularly when passing through occlusions which cannot be passed by guide wire 18.

The cutting bit 13 may be formed of any material that is biocompatible with blood. By way of example, stainless steel may be used to form a strong cutting bit capable of cutting through any form of atheroma. In some circumstances, particularly when softer clots are expected, a softer cutter is advantageous since it would be less likely to traumatize the vessel. For example, plastics such as polyurethane can be cast into cutting bits having a desired hardness, and a plurality of bits having differing hardness levels can be made available. By then observing the nature of the stenotic material, the optimum combination of cutter bit material, bit extension, and rotational speed can be selected to remove the stenotic material with minimum chance of damage to the blood vessel. Usually, such plastic cutting bits will be made radiopaque by the addition of a tantalum, gold, bismuth, or barium filling.

Vessel blockages can occur in a wide variety of forms, from very hard calcified material to very soft thrombus/clot material. Most peripheral muscles have collateral flow and a surprising amount of leg pain is tolerated. For these reasons, long total occlusions are fairly common. Flow rates and pressure are also much lower further from the heart which provide an opportunity for blood to sit, clot and form thrombus. In coronary arteries, however, it is unusual to see much thrombus due both to the high flow rate and pressure. Most heart attacks are not total occlusions but rather are the results of restricted flow (caused by a gradually tightening atheroma) combined with unusual exercise. Therefore, the clots within the coronary arteries are typically highly calcified. Since hard material such as stainless steel can be expected to provide stronger cutting edges, they would be more suitable for attacking the more calcified atheromas. In contrast, a softer plastic material could be used to cut through thrombus thereby lowering the risk of traumatizing the surrounding vessel.

The atherectomy device described herein is particularly suited for removing extended occlusions (stenosis) such as those associated with thrombus and atheromas. It is contemplated that the catheter will be introduced into the vascular system using traditional percutaneous or surgical techniques. Percutaneous techniques generally involve insertion of the catheter into remote occluded vessels through a conventional guiding catheter. Surgical techniques, in contrast, involve catheter insertion through a surgical incision, typically utilizing longer and/or less flexible catheter constructions.

The cutting bit 13 is adapted to recess within housing 11 when the atherectomy device is not in use. It is also contemplated that the cutting bit 13 will be withdrawn within housing 11 while the catheter is being introduced to the region of the occlusion. This is particularly important if it is being passed through tortuous vessels outside the confines of a guiding catheter so the bit will not be exposed to the fragile vessel walls. In such situations, recessing the bit significantly reduces the risks of traumatizing the vessel that would otherwise be associated with the devices's use.

It has been discovered that there is typically no need to place more than distal tip 20 of helical blade 50 itself outside of the confines of housing 11 in order to successfully remove an occlusion. In a preferred method of use, the blade 50 would be activated while still being recessed within housing 11. When softer thrombus-type materials are encountered, the vacuum generated by a rapidly spinning cutting bit 13 located just within housing 11 will create enough suction to draw thrombus material into contact with bit 13 thereby facilitating cutting.

To utilize the atherectomy device, it is contemplated that the atherectomy device will be inserted into a vessel such as a vascular (blood) vessel, using conventional insertion techniques. The cutter assembly 5 is then advanced through the vessel with the cutter recessed until cutting bit 13 is positioned adjacent the stenosis. Guide wire 18 is inserted into the vessel and advanced to the stenosis. The remainder of the atherectomy device 1 is then inserted over guide wire 18 until cutting assembly 5 is positioned adjacent the stenosis (typically within 1–3 cm). An attempt is made to advance guide wire 18 through as much of the stenosis as is safely possible. By advancing the cutting bit 13 over the guide wire 18, the likelihood of the cutting bit deviating from the desired cutting path is greatly decreased. Proper alignment of the cutting bit 13 is further assured by the trailing collection chamber 17 which stabilizes and centers the cutting bit. When relatively soft stenosis material is encountered, it is desirable to begin the cut with the cutting bit 13 completely recessed within housing 11. This is particularly desirable in view of the tendency of the cutting bit 13 to wander when passing through relatively soft material. The entire cutting assembly is then advanced through the vessel, cutting as it proceeds. As the bit 13 moves through the stenosis vessel, it is stopped periodically while an attempt is made to push guide wire 18 through the remainder of the occlusion. In view of the substantially reduced risks encountered by drill bits proceeding over a guide wire, it is desirable to check relatively often whether the guide wire 18 can pass further through the stenosis. The unexposed cutting bit 13 will not be able to pass through calcified materials. Therefore, if substantial resistance is met, the bit 13 is extended an incremental amount beyond the distal extremity of housing 11. After extension, another attempt is made to cut through the material. Over the course of an extended occlusion, it may be necessary to incrementally extend the drive cable several times thereby exposing more of the cutting bit 13. Such incremental movements are made by pushing thumb lever 31 forward. By using a conservative approach, the occlusion may be traversed with a minimally exposed bit 13 while making frequent attempts to pass guide wire 18 through the occlusion. Such an approach minimizes the risk of damaging the vessel.

The cutting bit 13 may be fashioned from any suitable material or combination of materials, so long as its leading edge may be formed into effective cutting edge and the material does not have any adverse health implications when placed within a bloodstream. There are a large number of metals, plastics and ceramics which could be used. An example of a suitable metallic cutter material is stainless steel. Metallic cutters have an advantage in that they are hard and tend to better retain their cutting edges during cutting. However, since it is contemplated that most atherectomy devices will only be used once, a long lasting cutting edge is not generally critical. Therefore, various plastic materials and the like which are softer than metals or ceramics may often be used, particularly in cases where the catheter will be advanced without the benefit of a guide wire and the stenotic material is sufficiently soft, e.g., clot or thrombus, to be removed by the plastic material. The softer materials have an advantage in that they are less traumatic to the vessel. When using metals or plastics, it may be desirable to provide a polytetrafluoroethylene (Teflon TM) coating to increase the lubricity of the cutting bit during use.

Particularly, when reducing stenosis within peripheral blood vessels, the external diameter of the intravascular portion of the atherectomy device may be sized very near the diameter of the vessel in order to stabilize the cutter. Particularly, tubular member 7, housing 11 and collection chamber 17 may be so sized.

An alternative embodiment of the cutter bit is shown in FIG. 5. In this embodiment, the cutter bit is in the form of a screw 60 which functions much the same as the blade 51 described in relation to FIG. 4. The screw 60, includes, however, only a single cutting thread 19 and helical channel 21. Since channels formed in a screw construction are substantially larger than those formed in drill bits, there is no need for fluting.

Referring now to FIGS. 6 and 7, a second embodiment of the atherectomy catheter of the present invention will be described. Atherectomy catheter 100 includes a flexible tubular member 102 having a proximal end 104, a distal end 106, and a central lumen 108 extending beyond the proximal and distal ends. The proximal end 104 of flexible tubular member 102 is secured to a proximal housing 110 which will be described in greater detail hereinafter. The distal end 106 of the tubular member 102 terminates in an open, circular port.

A first flexible drive cable 112 is disposed within the central lumen 108 of tubular member 102 and is capable of both axial and rotational movement therein. The drive cable 112 is itself a tubular structure having a central lumen 114 which extends its entire length. A second drive cable 116 is disposed within the central lumen 114 of first drive cable 112. The second drive cable 116 is free to rotate and axially translate relative to both the first drive cable 112 and the flexible tubular member 102.

Optionally, the second drive cable 116 may be a tubular member having a central lumen (not illustrated). This will be the case when the catheter 100 is intended to be inserted over a conventional guide wire 120.

A circular cutting blade 122, typically in the form of a tubular cutting blade having a honed distal end 124, is secured to the distal end of the first drive cable 112. Similarly, an anchor member 126, typically in the form of a helical screw, is secured to the distal end of the second flexible drive cable 116. Generally, the anchor member 126 will be disposed within interior lumen 128 of the tubular blade 122 (as illustrated in FIG. 7), but will be extendable so that it can project forward of both the tubular member 102 and the tubular blade member 122 (as illustrated in FIG. 6).

Proximal housing 110 includes an interior chamber 130 which receives the flexible drive cables 112 and 116 and is open to the lumen 108 of flexible tubular member 102. Side fittings 132 are optionally provided to allow external fluid communication with the chamber 130, which in turn allows for introduction of fluids into the lumen 108 of tubular member 102. In this way, fluids can be introduced into the blood vessel through the annular gap between flexible tubular member 102 and circular cutting blade 122. Fluid infusion will be particularly desirable when fluid aspiration is being performed through lumen 114 of drive member 112. It may also be advantageous to provide a pressure increase to counteract the centrifugal force created by rapid rotation of anchor 126 as described below.

The flexible guide cables 112 and 116 extend out the proximal end of housing 112 through a threaded fitting 134 which provides a rotatable seal to prevent the leakage of fluids from the interior chamber 130. The first drive cable 112 terminates in a drive shaft 140 and thumb lever 142, both of which are similar to the constructions described in reference to FIG. 2 above. That is, a motorized means (not shown) can be used to rotate the first drive cable 112 (as indicated by arrow 144) while the thumb lever 142 is utilized to axially position the drive cable 112. Rotating and axially translating the drive cable 112, of course, causes corresponding rotation and axial movement in the tubular blade 122.

Second drive cable 116 terminates in a drive shaft 150 and thumb lever 152. Drive shaft 150 and thumb lever 152, in turn, can be utilized as described above to rotate and axially translate the second drive cable 116. Such rotation and translation in turn rotate and translate the anchor member 126. Rotation and axial translation of both the tubular member 122 and the anchor member 126 may be achieved independently both of each other and of the flexible tubular member 102.

The construction of the anchor member 126 should be sufficient to allow the anchor member to be advanced and embedded into the region of stenosis in the blood vessel. The helical screw design illustrated is generally the most convenient and useful, although other constructions might also find use. Generally, rotation of the anchor 126 will be at a low rpm so that positioning within the center of the stenosis can be carefully controlled. Indeed, the anchor 126 can be repositioned as necessary until an optimum location is achieved.

Referring now to FIGS. 8A–8D, the method of the present invention employing the catheter of FIGS. 6 and 7 will be described. Initially, catheter 100 is positioned within blood vessel BV, conveniently over a guide wire 120. Positioning of the guide wire 120 and the catheter 100 is entirely conventional and need not be described further. The catheter 100 will be inserted until distal end 106 lies immediately adjacent the region of stenosis S.

Referring now to FIG. 8B, the helical screw anchor member 126 will be advanced into the region of stenosis S by rotating and axially advancing the second drive cable 116. The anchor member 126 will be advanced sufficiently so that it is secured or embedded within the stenosis S and able to serve as an anchor for the remaining catheter operations. Usually, rotation and advancement will be accomplished manually as low speed operation will be utilized.

Referring now to FIG. 8C, once the anchor 126 is in place, tubular blade 122 will be advanced over the anchor member 126 by rotating and axially advancing the first drive cable 112. The anchor member 126 will act as a guide in directing the blade 122 generally down the center of the lumen of the blood vessel BV. Rotation of the blade 122 may be performed at much higher rpm, typically in the range from 1000 to 2500 rpm, in order to assure even cutting. As the anchor is in place, the risk of damage to the blood vessel is greatly reduced. In particular, by fluoroscopically checking the position of the anchor 126 prior to advancing the blade 122, trauma to the blood vessel from the blade can almost always be avoided.

The anchor member 126 and the tubular blade 122 will interact to entrap the severed stenosis material therebetween, thus preventing the release of emboli into the blood vessel. Once the blade 122 has been advanced partially or fully through the region of stenosis S, the blade and anchor member may be simultaneously retracted into the flexible tubular member 102, as illustrated in FIG. 8D. The anchor member 126 and blade 122 can then be withdrawn through the tubular member 102, the anchor cleaned of stenotic material, and the anchor and blade reintroduced to the patient. Alternatively, the tubular member may be used for aspiration of clot or thrombus once a region of plaque has been removed. In either case, the tubular member 102 will generally not be removed until the entire procedure is completed.

Although only a few embodiments of the present invention have been described, it should be understood that the present invention may be embodied in many other specific forms without departing from the spirit or scope of the invention. Particularly, it should be appreciated that the specific proximal actuator assembly disclosed can be widely varied to effect the required motions for the drive cable. Similarly, the specific construction of both the drill bit as well as the materials from which the bit is fashioned may be widely varied within the teachings of the present invention in order to suit a particular application.

The catheter 100 may also be operated in a continuous manner where the tubular blade 122 and anchor member 126 are simultaneously advanced through a region of stenosis, typically a soft atheroma, clot, or thrombus. Referring to FIGS. 9A and 9B, the relative axial positions of the blade 122 and anchor member 126 are fixed (e.g., by securing levers 142 and 152), with the tip of member 126 usually but not necessarily extending distally beyond the blade 122, typically from about 1 to 10 mm beyond the distal end of the blade. Usually, the blade 122 will not be rotated, while the anchor member 126 is rotated at a medium speed, typically below 100 RPM. The blade 122 and anchor 126 are then advanced, optionally over guide wire 120, to enlarge the vessel lumen through stenosed region S. By maintaining relative rotation between blade 122 and anchor 126, the stenotic material S drawn into the distal end of blade 122 is severed by the base threads of the anchor as they rotate past the blade 122. Such severing provides a smooth surface alaong the entire length of the enlarged lumen.

Referring now to FIG. 10, additional design variations of the atherectomy catheter of the present invention will be described. The catheter 150 comprises a flexible tubular member 152, a tubular cutting blade 154 mounted within the distal end of tubular drive member 156, and an anchor member 158 mounted on the distal end of drive cable 160. As described thus far, the catheter 150 is substantially similar to catheter 100 described previously.

The modifications in catheter 150 over catheter 100 are as follows. An inflatable balloon 162 is connected to an inflation lumen 164 formed in the wall of tubular member 152 so that the balloon may be inflated from the proximal end (not illustrated) of the catheter. The balloon 162 is useful in aligning the catheter 150 so that the blade 154 and anchor 158 may be directed centrally down the lumen to be treated. The tubular member 152 is rotated (preferably the member will be attached to its proximal housing by a rotary coupling member as described previously), and the balloon 162 inflated to provide a desired tip deviation. The blade 154 and anchor 158 may then be extended by either of the techniques (incremental or continuous) described above.

In a second modification, a screen 166 is disposed in the distal end of cutting blade 154. The screen 166 will be useful if aspiration is employed to drawn stenotic material back through the lumen of drive member 156. The screen 166 will trap large pieces of stenotic material (which would otherwise tend to plug the lumen of drive member 156), but allow small pieces to be aspirated proximally. By providing a gap 168 between the screen 166 and the lumen wall of the blade 154, aspiration at the distal tip of blade 154 will continue even after large amounts of stenotic material have been captured.

A third modification comprises forming a side aperture 170 in the anchor member 158. The aperture may be positioned on non-symetric, e.g., eliptical, lesions to allow removal of a greater amount of material in a single pass of cutting blade 154.

Additionally, the mounting for the guide wire and drive cable within the tubular member may be widely varied and other features such as angioplasty balloons may be incorporated into the catheter design proximally to the cutter, Therefore, the present examples and embodiments are to be considered as illustrative and not restrictive, and the invention is not to be limited to the details given herein, but may be modified within the scope of the appended claims.

We claim:

1. An atherectomy device comprising:
   a flexible tubular member having proximal and distal ends and a central lumen extending therebetween;
   a flexible drive member rotatably disposed in the central lumen of the flexible tubular member;
   a collection chamber having an open distal end, said collection chamber being detachable secured to and isolated from the distal end of the flexible tubular member, whereby stenosis is not received in the flexible tubular member and the collection chamber can be removed to allow cleaning; and
   a helical blade having a blade tip and a shank attached to a distal end of the flexible drive member, said blade being disposed so that the blade tip can extend distally through the open distal end of the collection chamber while the blade shank remains within the collection chamber, whereby stenosis may be severed and translated proximally into the collection chamber through the open distal end by rotating the blade.

2. An atherectomy device as in claim 1, further comprising means secured to the flexible drive member for rotating and axially translating said flexible drive member, whereby the helical blade may be moved between a retracted position where the blade tip is within the collection chamber and an extended position where the blade tip is outside of the chamber while the blade shank is within the chamber.

3. An atherectomy device as in claim 1, wherein the collection chamber includes a rigid distal housing segment and a resilient proximal body segment.

4. An atherectomy device as in claim 1, wherein the helical blade includes a pair of blade elements which meet at an angle in the range from about 55° to 65° at the blade tip.

5. An atherectomy device as in claim 4, wherein the helical blade has a helix angle in the range from 10° to 25°.

6. An atherectomy device as in claim 1, wherein the drive member and helical blade have aligned lumens capable of being introduced over a guide wire.

7. An atherectomy device comprising:
   a flexible tubular member having proximal and distal ends and a central lumen extending therebetween;
   a first flexible drive cable rotatably disposed in the central lumen of the flexible tubular member, said cable having proximal and distal ends and a central lumen extending therebetween;
   a circular blade having an open distal end secured to the distal end of the first flexible drive cable;
   a collection screen disposed within the open distal end of the cutting blade;
   a second flexible drive cable rotatably disposed in the central lumen of the first flexible drive cable, said second cable having proximal and distal ends;
   an anchor member secured to a distal end of the second flexible drive cable; and
   means for rotating and advancing the first and second flexible drive cables, said means being secured to said drive cables.

8. An atherectomy device as in claim 7, wherein the anchor member is a screw.

9. An atherectomy device as in claim 8, wherein the outside diameter of the screw is approximately the same as the inside diameter of the circular cutting blade.

10. An atherectomy device as in claim 7, wherein the cutting blade is an elongate tube.

11. An atherectomy device as in claim 7, further comprising a proximal housing attached to the flexible tubular member.

12. An atherectomy device as in claim 7, wherein the second flexible drive cable and the anchor member have axially aligned central lumens capable of receiving a guide wire.

13. An atherectomy catheter as in claim 7, further comprising an inflatable balloon secured to one side of the distal end of the flexible tubular member, whereby the catheter tip may be transversely deviated by inflating the balloon.

14. An atherectomy catheter as in claim 7, wherein a side aperture is formed in the anchor member to provide for enhanced removal of stenotic material.

15. A method for performing atherectomy, said method employing a catheter including flexible tubular member, a tubular cutting member disposed in a lumen of the first tubular member, an anchor member disposed in a lumen of the circular cutting member, and a collection screen within the tubular cutting blade, said method comprising:
   introducing the catheter into a blood vessel proximate a region of stenosis;
   advancing the anchor from the catheter member into the stenosis so that the anchor becomes embedded therein;
   advancing the tubular cutting member from the catheter over the anchor so that a portion of the stenosis is severed and entrapped between the cutting member and the anchor and within the collection screen; and
   simultaneously retracting the anchor and the cutting member into the catheter in order to remove the severed stenosis from the blood vessel.

16. A method as in claim 15, wherein the catheter is introduced to the blood vessel over a guide wire.

17. A method as in claim 15, wherein the anchor is a screw which is advanced into the stenosis by rotation.

18. A method as in claim 15, wherein the severed stenosis is entrapped between the threads of the screw and the cutting member by rotating the cutting member as it is advanced.

19. A method as in claim 17, wherein the anchor and tubular cutting member are advanced simultaneously, with the anchor being rotated and the cutting blade not being rotated, whereby stenotic material is continuously severed and translated proximally into the tubular cutting member.

* * * * *